(12) United States Patent
Steiner et al.

(10) Patent No.: US 9,588,093 B2
(45) Date of Patent: Mar. 7, 2017

(54) DEVICE FOR DETERMINING THE $H_2$ CONTENT OF $H_2$/NATURAL GAS MIXTURES

(71) Applicant: Robert Bosch GmbH, Stuttgart (DE)

(72) Inventors: Dietmar Steiner, Welzheim (DE); Pedro Da Silva, Kirchheim (DE)

(73) Assignee: Robert Bosch GmbH, Stuttgart (DE)

( * ) Notice: Subject to any disclaimer, the term of this patent is extended or adjusted under 35 U.S.C. 154(b) by 297 days.

(21) Appl. No.: 14/554,831

(22) Filed: Nov. 26, 2014

(65) Prior Publication Data
US 2015/0143873 A1 May 28, 2015

(30) Foreign Application Priority Data
Nov. 27, 2013 (DE) .................. 10 2013 224 246

(51) Int. Cl.
*G01N 33/00* (2006.01)
*G01N 27/407* (2006.01)

(52) U.S. Cl.
CPC ....... *G01N 33/005* (2013.01); *G01N 27/4074* (2013.01)

(58) Field of Classification Search
USPC ................... 73/23.2, 30.03, 31.05
See application file for complete search history.

(56) References Cited

U.S. PATENT DOCUMENTS

| | | | |
|---|---|---|---|
| 7,174,768 B2* | 2/2007 | Ito .................. | G01N 33/005 73/25.01 |
| 7,661,304 B2* | 2/2010 | Konzelmann ........ | G01N 25/18 73/204.26 |
| 8,821,797 B2* | 9/2014 | Tsukabayashi ...... | G01N 27/16 422/83 |
| 2012/0040264 A1* | 2/2012 | Maslyn ............. | H01M 8/04343 429/432 |
| 2015/0160163 A1* | 6/2015 | Yamamoto .......... | G01N 27/66 73/30.04 |
| 2015/0301010 A1* | 10/2015 | Valentini ........... | G01N 33/203 73/19.07 |

* cited by examiner

Primary Examiner — Eric S McCall
(74) Attorney, Agent, or Firm — Maginot, Moore & Beck LLP

(57) ABSTRACT

A device for determination of the $H_2$ content of $H_2$/natural gas mixtures comprises an input interface configured to read in a calorific value of a first $H_2$/natural gas mixture from a delivery station of a gas grid, an input interface configured to introduce a second $H_2$/natural gas mixture into the device; a proton-conducting layer fluidically connected to the input interface of the second $H_2$/natural gas mixture and configured to permit determination of a current-voltage characteristic, a volumetric flow rate sensor configured to determine a volumetric flow rate of the second H2/natural gas mixture into the proton-conducting layer, and a control apparatus connected to the proton-conducting layer, the input interface of the second $H_2$/natural gas mixture, and the volumetric flow sensor. The control apparatus is configured to determine whether there is a hydrogen depletion of the proton-conducting layer, and output the current calorific value of the second $H_2$/natural gas mixture.

10 Claims, 3 Drawing Sheets

«DEVICE FOR DETERMINING THE $H_2$ CONTENT OF $H_2$/NATURAL GAS MIXTURES»

This application claims priority under 35 U.S.C. §119 to patent application no. DE 10 2013 224 246.8, filed on Nov. 27, 2013 in Germany, the disclosure of which is incorporated herein by reference in its entirety.

BACKGROUND

If the fraction of renewable energy in the German power market develops further in accordance with the concepts of the legislator, volatile, fluctuating sources of energy generation such as, for example, wind power or photovoltaics, from the year 2030 will provide more than 60% of the power requirement in Germany. If these sources in times of copious wind and sun with simultaneously low demand on the sides of the consumer are not to be down-regulated or even at times taken out of operation, then a store for receiving the surplus electrical energy will be required. A technically achievable and economically feasible possibility is offered for this purpose by the electrolytic generation of hydrogen from renewable electrical energy and the subsequent introduction thereof into the already existing gas grid or gas stores, which is also known as the concept "power to gas". Currently, a content of 5% of $H_2$ in the gas grid is permitted, and an increase to a content of 10% is under discussion against the background of the required storage function. However, mixtures of $H_2$ and natural gas, owing to the lower volumetric energy density of $H_2$ ($H_u$=3 kWh/m³ S.T.P.) in comparison with that of natural gas ($H_u$~10 kWh/m³ S.T.P.), have a lower heating value than pure natural gas.

The heating value/calorific value of natural gas mixtures ($CH_4$, $C_2H_6$, $C_3H_8$ etc. and $H_2$) is currently determined in what are termed delivery stations of the gas grid using cost-intensive multichannel gas chromatography measuring chambers, the cost of which exceeds 100,000 C. If, now, downstream of a delivery station, $H_2$ is fed into the local distribution grid by a local energy producer, then at the consumers, in each case local calorific value sensors must be used in order to be able to determine the variable current calorific value of the $H_2$/natural gas mixture with sufficient accuracy. In addition, the operating parameters of a gas heater depend on the chemical composition of the fuel gas provided, for which reason the engine control of the gas engines of combined heat and power plants, for an energetically optimal combustion, requires knowledge of the current composition of the fuel gas provided (in this case, in particular, the content of hydrogen in the $H_2$/natural gas mixture). However, the multichannel gas chromatograph is too expensive for both tasks.

SUMMARY

In one embodiment, the present disclosure is directed to a device for determining the $H_2$ content of $H_2$/natural gas mixtures has the advantage that henceforth, locally, on the part of the end consumer, the calorific value of the $H_2$/natural gas mixture taken can be measured qualitatively in a high grade manner and simultaneously inexpensively, in order thereby to implement the required operating parameters of a gas heater for a variable composition of the provided fuel gas in the best manner possible. The variable composition of the provided fuel gas, in particular with respect to the content of $H_2$, results in the event that, in the context of the "power to gas" initiative, electrolytically generated hydrogen from what are termed renewable energy sources, such as, for example, wind power or photovoltaics, is fed into the local low-pressure grid, that is to say between the delivery station and the end consumer, which has not been recorded to date by instrumentation.

The present device in one embodiment, in comparison with the multichannel gas chromatographs known to date, is a considerably simpler measurement technique for use at an end consumer, in which, in the first step, the $H_2$ content of an $H_2$/natural gas mixture is determined at the end consumer, and in the second step, on the basis of this knowledge, and the calorific value of the $H_2$/natural gas mixture, which was determined at a delivery station of the gas grid, the current calorific value for the $H_2$/natural gas mixture is then determined. Particularly advantageous in the case of the present device, is the case that, thereby, the current calorific value can be determined with approximately 0.3% accuracy, in such a manner that a technically optimum operation can be implemented for the gas heater in the case of variable composition of the fuel gas provided. The inexpensive and accurate determination of the current calorific value in the present device is achieved primarily by the use of components from automobile technology (such as, for example, a hot-film mass sensor, a PEM fuel cell), which on account of the ready availability in large numbers, can be offered inexpensively and in a high quality grade.

Furthermore, using the present device of one embodiment, the external power supply of the device may advantageously be minimized by the electrochemical conversion of the hydrogen into electrical power in a downstream fuel cell. In a further optimized system design it could—buffered by an accumulator—even be dispensed with completely.

The present disclosure relates to a measuring device which determines the hydrogen content in an $H_2$/natural gas mixture. Against the background of a known-transmitted via the delivery station—calorific value, the present device then calculates the current or local calorific value downstream of the delivery station, that is to say the end consumer, on the basis of the measured hydrogen content. The calorific value determined by the delivery station in this case is preferably transmitted telemetrically (for example by wireless, the GSM network or a telephone line) to the present device. The hydrogen content is determined in the present device in a modification of a technology which is used for separating off the hydrogen from an $H_2$/natural gas mixture and is known as what is termed an "electrochemical hydrogen separator". For this purpose, a PEM fuel cell is used as an electrochemical hydrogen pump. A PEM fuel cell in this case is able via electrochemical pumping to separate hydrogen from, for example, a methane/hydrogen mixture.

It has been found that the shape of the current-voltage characteristic for the electrochemical hydrogen pump is dependent on the hydrogen content of the gas mixture introduced. From a certain critical current density, on account of the anode-side depletion of hydrogen, the anode potential increases greatly. The height of the critical current density depends substantially on the $H_2$ concentration of the gas mixture. Above a certain $H_2$ concentration, which is dependent on the type of the PEM fuel cell (for example 25%), for a maximum possible volumetric flow rate through the PEM fuel cell, hydrogen depletion no longer occurs. By controlling the gas flow at the anode side, the hydrogen depletion could also still be observed at a higher concentration of hydrogen, or, at lower concentrations, a higher measurement accuracy could be achieved. For assigning the critical current density to a certain $H_2$ concentration in the gas mixture, in this case, knowledge of the volumetric flow rate through the anode is of relevance.

In the method for determining the $H_2$ content of the $H_2$/natural gas mixture, firstly the $H_2$ content is determined roughly in the anode gas or via the proton-conducting layer, that is to say a determination is made, in particular, as to whether, at the present volumetric flow rate of the $H_2$/natural gas mixture through the proton-conducting layer, a hydrogen depletion of the proton-conducting layer occurs. Thereafter, the volumetric flow rate of the anode gas is controlled in such a manner that the drop in the current-voltage characteristic can still readily be observed, that is to say it is still certain that depletion of the $H_2$ at the anode occurs. The connection between the critical current density and the $H_2$ content of the anode gas is deposited for various volumetric flow rates of the anode gas in a characteristic diagram of an associated control apparatus of the device. The hydrogen content of the $H_2$/natural gas mixture is therefore determinable to an accuracy of <1%. Since the calorific value of $H_2$ is only ~30% of the calorific value of natural gas, the calorific value of the $H_2$/natural gas mixture is determinable to an accuracy of less than 0.3%.

According to a further embodiment of the present device, in addition, a sensor can be provided for measuring the temperature of the volumetric stream of the $H_2$/natural gas mixture into the proton-conducting layer which is connected to the control apparatus. This leads advantageously to a further increase in the accuracy of measurement of the present device when in addition the fluctuating gas density at variable temperature of the introduced $H_2$/natural gas mixture is taken into account.

According to a further embodiment of the present device, it can be fluidically coupled to a gas line in the manner of a bypass. The flux of the $H_2$/natural gas mixture in the gas line to the combustion chamber of the gas heater is not thereby interfered with by a resistance in the gas line.

According to a further embodiment of the present device, the sensor for measuring the volumetric flow rate of the $H_2$/natural gas mixture into the proton-conducting layer can be a hot-film mass sensor, a flow regulator or a critical nozzle. For the flow regulator, any flow regulator known from the prior art can be used. In particular, for determining the $H_2$ content from the critical current density, the volumetric flow rate of the $H_2$/natural gas mixture into the proton-conducting layer or into the anode of the electrochemical hydrogen pump must be measured.

According to a further embodiment of the present device, the proton-conducting layer can be a component of a PEM fuel cell which is configured as an electrochemical hydrogen pump, and has an interface for channeling hydrogen, and an interface for channeling the natural gas mixture without hydrogen out of the PEM fuel cell.

According to a further embodiment of the present device, the interface for channeling hydrogen can be coupled to a device for converting hydrogen into electrical power, to the gas grid, or to a consumer for hydrogen. The pure hydrogen exiting at the cathode of the electrochemical hydrogen pump is then subsequently converted into electrical power, for example, in a downstream fuel cell, a gas geyser or a combined heat and power plant, or fed to the gas grid or a consumer for hydrogen for further energetic utilization.

According to a further embodiment of the present device, the interface for channeling the natural gas mixture without hydrogen can be coupled to the gas grid or to a device for converting the natural gas mixture without hydrogen into heat. The natural gas mixture of the anode of the electrochemical hydrogen pump cleaned of hydrogen is reintroduced into the gas grid or burnt in a downstream consumer.

According to a further embodiment of the present device, the proton-conducting layer can be a Nafion membrane and can be moistened for determining the current-voltage characteristic. The Nafion membrane of the PEM fuel cell must be moistened, which can be achieved, for example, by means of an external moistening unit.

According to a further embodiment of the present device, the PEM fuel cell can be fluidically coupled via the interface for channeling hydrogen to a second PEM fuel cell, wherein the second PEM fuel cell takes up hydrogen from the PEM fuel cell and converts it into water which is provided for moistening the PEM fuel cell and the second PEM fuel cell. The Nafion membrane of the PEM fuel cell (that is to say the electrochemical hydrogen pump or the pump cell) and also the downstream second PEM fuel cell (what is termed the "disposal cell") must be moistened. The water can in part be taken over from the resulting product water of the disposal cell. Alternatively, for this purpose, an external moistening unit can be provided. The cathode of the downstream disposal cell must be supplied with cooling air, optionally via a fan.

According to a further embodiment of the present device, it can be coupled to a gas valve which is connected to the control apparatus and the determination of the current calorific value of the $H_2$/natural gas mixture proceeds permanently or temporarily. In this case, the device can additionally be provided with an interface for receiving information with respect to the currently generated amount of hydrogen of the individual producers of hydrogen between the delivery station and the end consumer, in order in this manner to adapt in a targeted manner the frequency of the measurement of the actual calorific value of the $H_2$/natural gas mixture. If the $H_2$/natural gas mixture was odorized with sulfur-containing compounds, then the sulfur must be removed via an upstream activated carbon adsorber.

The present disclosure will be described with reference to the accompanying drawings.

DETAILED DESCRIPTION

Figure 1:
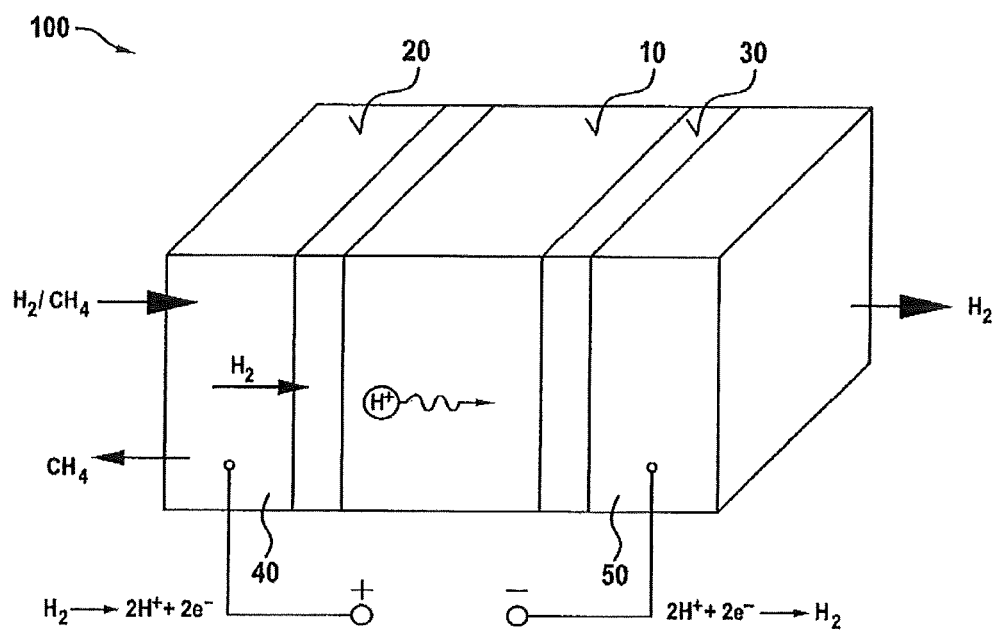
FIG. 1: shows a perspective view of a PEM fuel cell for use as an electrochemical hydrogen pump in a device for determining the $H_2$ content of $H_2$/natural gas mixtures according to the present disclosure.

FIG. 1 shows a perspective view of a PEM fuel cell 100 for use as an electrochemical hydrogen pump in a device (which is not shown) for determining the $H_2$ content of $H_2$/natural gas mixtures according to the present disclosure.

The PEM fuel cell 100 of the present disclosure is a measuring device which determines the hydrogen content in an $H_2$/natural gas mixture. Against the background of a known—transmitted by the delivery station (which is not shown)—calorific value, the present device then calculates the current calorific value downstream of the delivery station, that is to say the end consumer, on the basis of the measured hydrogen content. The calorific value determined by the delivery station in this case is preferably transmitted telemetrically (for example by wireless, the GSM grid or a telephone line) to the present device. The hydrogen content is determined in the present device in a modification of a technology which is used for separating off the hydrogen from an $H_2$/natural gas mixture and is known as what is termed an "electrochemical hydrogen separator". For this purpose, the PEM fuel cell 100 is used as an electrochemical hydrogen pump (also as what is termed a "pump cell"). The PEM fuel cell 100 in this case is able via electrochemical pumping to separate hydrogen from, for example, a methane/hydrogen mixture.

For this purpose, the PEM fuel cell 100 has a proton-conducting layer 10 in the manner of a Nafion membrane and is moistened to determine the current-voltage characteristic. The PEM fuel cell 100 consists of a diffusion layer 20 and a catalyst layer 30, wherein the Nafion membrane is arranged therebetween. On the input side, into the PEM fuel cell 100, in the region of the anode 40 thereof, the $H_2$/natural gas mixture is introduced which then passes through the Nafion membrane and adjacently to the catalyst layer 30 in the region of the cathode 50 of the PEM fuel cell 100 then exits as pure hydrogen in gas form. In the region of the anode 40, a volumetric flow rate of the natural gas mixture without hydrogen can be removed from the PEM fuel cell 100.

In this case, the shape of the current-voltage characteristic of the PEM fuel cell 100 for the electrochemical hydrogen pump is dependent on the hydrogen content of the gas mixture introduced. From a certain critical current density, on account of the anode-side depletion of hydrogen, the anode potential increases greatly. The height of the critical current density depends substantially on the $H_2$ concentration of the gas mixture introduced. Above a certain $H_2$ concentration, which is dependent on the type of the PEM fuel cell 100 (for example 25%), for a maximum possible volumetric flow rate through the PEM fuel cell 100, hydrogen depletion no longer occurs. By controlling the gas flow at the anode side, the hydrogen depletion could also still be observed at a higher concentration of hydrogen, or, at lower concentrations, a higher measurement accuracy could be achieved. For assigning the critical current density to a certain $H_2$ concentration in the gas mixture, in this case, knowledge of the volumetric flow rate through the anode is of relevance.

Figure 2:
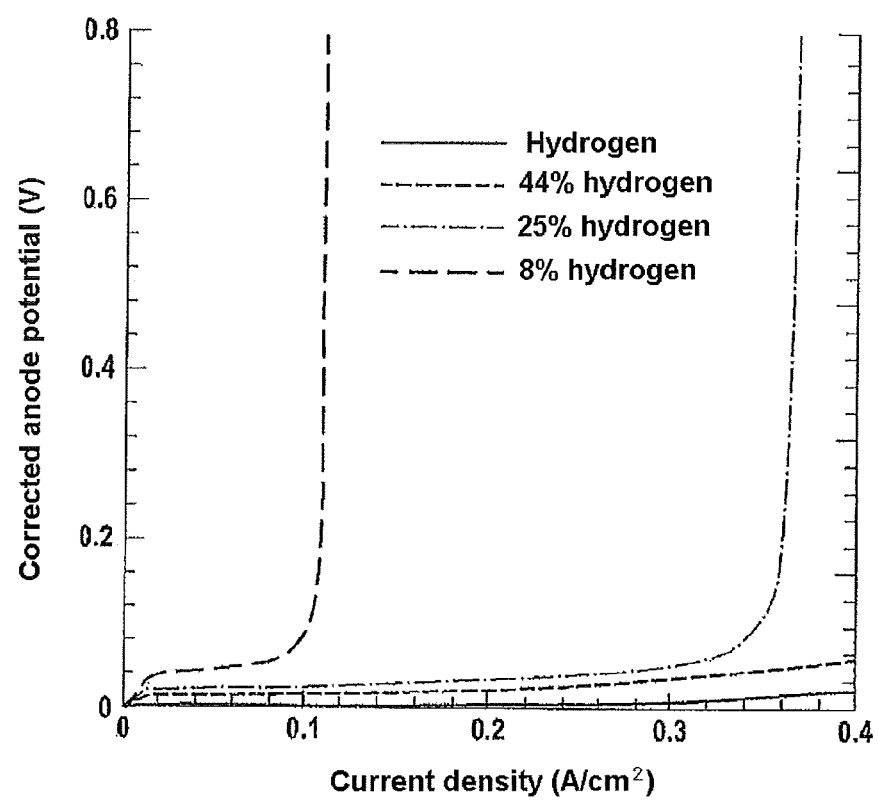
FIG. 2: shows a diagram to illustrate the connection between the corrected anode potential and the current density at different contents of hydrogen in an $H_2$/natural gas mixture which flows through the electrochemical hydrogen pump according to FIG. 1, and FIG. 3: shows a schematic view of a second PEM fuel cell which, to generate electrical power, is fluidically coupled to the PEM fuel cell according to FIG. 1.

FIG. 2 shows a diagram for illustrating the connection between the corrected anode potential and the current density at different contents of hydrogen in an $H_2$/natural gas mixture which flows through the electrochemical hydrogen pump according to FIG. 1. The measured values shown were measured on a PEM fuel cell (which is not shown) which has a 25 cm$^2$ size Nafion membrane, wherein the $H_2$/natural gas mixture was flushed through the anode (which is not shown) at 5 ml/s, and the cathode (which is not shown) was moistened by 2.3 ml/s of water.

In the present implemented method for determining the $H_2$ content of the $H_2$/natural gas mixture in the present device, firstly the $H_2$ content is determined roughly in the anode gas or via the proton-conducting layer (which is not shown), that is to say a determination is made, in particular, as to whether, at the present volumetric flow rate of the $H_2$/natural gas mixture through the proton-conducting layer, a hydrogen depletion of the proton-conducting layer occurs. Thereafter, the volumetric flow rate of the anode gas is controlled in such a manner that the drop in the current-voltage characteristic for the proton-conducting layer can still readily be observed, that is to say it is still certain that depletion of the $H_2$ at the anode occurs. The connection between the critical current density and the $H_2$ content of the anode gas is deposited for various volumetric flow rates of the anode gas in a characteristic diagram of an associated control apparatus (which is not shown) of the device. The hydrogen content of the $H_2$/natural gas mixture is therefore determinable to an accuracy of less than 1%. Since the calorific value of $H_2$ is only ~30% of the calorific value of natural gas, the calorific value of the $H_2$/natural gas mixture is determinable to an accuracy of less than 0.3%.

Figure 3:
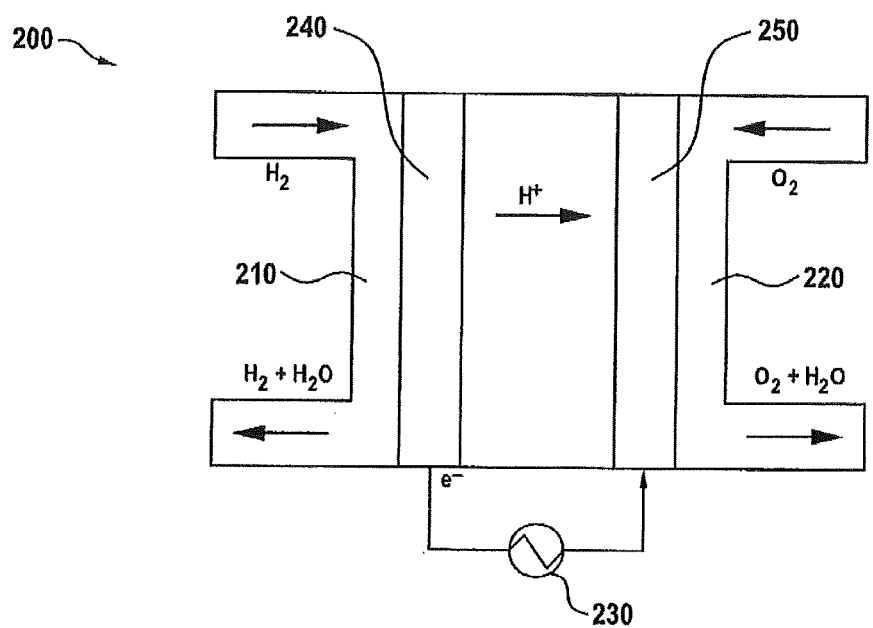

FIG. 3 shows a schematic view of a second PEM fuel cell 200 which is fluidically coupled to generate electrical power to the PEM fuel cell (the pump cell, which is not shown) according to FIG. 1. The electrochemically separated hydrogen from the PEM fuel cell is passed from the cathode thereof (which is not shown) into the anode chamber 210 of the downstream PEM fuel cell 200 (what is termed the "disposal cell") and there converted into electrical energy and water. The cathode chamber 220 is arranged opposite to the anode chamber 210. The electrical energy generated can be tapped at an interface 230. The anode 240 is arranged adjacently to the anode chamber 210, and the cathode 250 is arranged adjacently to the cathode chamber 220 in the interior of the second PEM fuel cell 200.

An example calculation for 8% and 25% $H_2$ content in the $H_2$/natural gas mixture shows, that even at an assumed electrical efficiency of the second PEM fuel cell 200 of only 30%, more electrical energy is generated than the pump cell consumes. At a corresponding dimensioning of the present measuring device, electrical energy for a hot-film measuring sensor (which is not shown) in the pump cell, a fan (which is not shown) for the PEM fuel cells and a control apparatus (which is not shown) would even still be available for controlling the device. The resultant water can take over a part of the moistening of the two Nafion membranes for the pump cell and the disposal cell. Alternatively, the separated hydrogen from the pump cell, however, can also be reintroduced via a fan into the gas grid (which is not shown), or can be burnt in a downstream consumer (which is not shown), such as, for example, a gas geyser or a combined heat and power plant.

What is claimed is:

1. A device for determining $H_2$ content of an $H_2$/natural gas mixture comprising:
   an input interface configured to read in a calorific value of a first $H_2$/natural gas mixture from a delivery station of a gas grid;
   an input interface configured to introduce a second $H_2$/natural gas mixture into the device;
   a proton-conducting layer fluidically connected to the input interface of the second $H_2$/natural gas mixture and configured to permit determination of a current-voltage characteristic;
   a volumetric flow rate sensor configured to determine a volumetric flow rate of the second $H_2$/natural gas mixture flowing into the proton-conducting layer;
   a control apparatus connected to the proton-conducting layer, the input interface of the second $H_2$/natural gas mixture, and the volumetric flow sensor, the control apparatus configured to:
   (i) determine, using the current-voltage characteristic of the proton-conducting layer, whether the proton-conducting layer has a hydrogen depletion at a volumetric flow rate of the second $H_2$/natural gas mixture, wherein if the control apparatus determines that the proton-conducting layer does not have a hydrogen depletion, the control apparatus changes the volumetric flow rate of the second $H_2$/natural gas mixture and again determines, using the current-voltage characteristic of the proton-conducting layer, whether the proton-conducting layer has a hydrogen depletion after the volumetric flow rate has been changed;

wherein, if the control apparatus determines that the proton-conducting layer has a hydrogen depletion, the control apparatus determines a critical current density of the proton-conducting layer at which the hydrogen depletion of the proton-conducting layer occurs with an associated measured volumetric flow rate of the second $H_2$/natural gas mixture;

(ii) establish, using a characteristic diagram, $H_2$ content of the second $H_2$/natural gas mixture based on the determined critical current density;

(iii) determine a current calorific value of the second $H_2$/natural gas mixture based on the established $H_2$ content of the second $H_2$/natural gas mixture and the calorific value of the first $H_2$/natural gas mixture from the delivery station of the gas grid; and (iv) output the current calorific value of the second $H_2$/natural gas mixture.

2. The device for determining $H_2$ content of an $H_2$/natural gas mixture according to claim 1, further comprising:
a temperature sensor connected to the control apparatus and configured to measure a temperature of the second $H_2$/natural gas mixture flowing into the proton-conducting layer.

3. The device for determining $H_2$ content of an $H_2$/natural gas mixture according to claim 1, wherein the proton-conducting layer is fluidically connected to a gas line via a bypass.

4. The device for determining $H_2$ content of an $H_2$/natural gas mixture according to claim 1, wherein the volumetric flow rate sensor is one of a hot-film mass sensor, a flow regulator and a critical nozzle.

5. The device for determining $H_2$ content of an $H_2$/natural gas mixture according to claim 1, wherein:

the proton-conducting layer is fluidically connected to a gas valve which is connected to the control apparatus; and the calorific value of the second $H_2$/natural gas mixture is determined permanently or temporarily.

6. The device for determining $H_2$ content of an $H_2$/natural gas mixture according to claim 1, further comprising:
a first PEM fuel cell configured as an electrochemical hydrogen pump, the proton-conducting layer being a component of the first PEM fuel cell, the first PEM fuel cell including an interface configured to channel hydrogen and an interface configured to channel a natural gas mixture without hydrogen.

7. The device for determining $H_2$ content of an $H_2$/natural gas mixture according to claim 6, wherein the interface configured to channel hydrogen is coupled to: (i) a device configured to convert hydrogen into electrical power; (ii) the gas grid; or (iii) a consumer for hydrogen.

8. The device for determining $H_2$ content of an $H_2$/natural gas mixture according to claim 6, wherein the interface configured to channel the natural gas mixture without hydrogen is coupled to: (i) the gas grid; or (ii) a device configured to convert the natural gas mixture without hydrogen into heat.

9. The device for determining $H_2$ content of an $H_2$/natural gas mixture according to claim 6, wherein the proton-conducting layer is a Nafion membrane and is configured to be moistened in order for the current-voltage characteristic to be determined.

10. The device for determining $H_2$ content of an $H_2$/natural gas mixture according to claim 9, further comprising:
a second PEM fuel cell fluidically coupled to the first PEM fuel cell via the interface configured to channel hydrogen, the second PEM fuel cell configured to take up hydrogen from the first PEM fuel cell and convert the hydrogen taken up from the first PEM fuel cell into water so as to provide moistening of the first PEM fuel cell and the second PEM fuel cell.

* * * * *